United States Patent [19]

Bäder et al.

[11] Patent Number: 5,710,333
[45] Date of Patent: Jan. 20, 1998

[54] PROCESS FOR THE PREPARATION OF TERTIARY AMINE OXIDES

[75] Inventors: Georg Bäder, Hofheim, Germany; Ramon Joglar Tamargo, Tarragona, Spain

[73] Assignee: Hoechst Aktiengesellschaft, Germany

[21] Appl. No.: 693,915

[22] Filed: Aug. 6, 1996

[30] Foreign Application Priority Data

Aug. 7, 1995 [DE] Germany .................. 195 28 945.5

[51] Int. Cl.$^6$ .................................................. C07C 291/04
[52] U.S. Cl. ................................................ 564/298; 564/297
[58] Field of Search .................................. 564/297, 298

[56] References Cited

U.S. PATENT DOCUMENTS

| | | | |
|---|---|---|---|
| 3,215,741 | 11/1965 | Chadwick | 260/583 |
| 3,283,007 | 11/1966 | Chadwick | 260/583 |
| 3,432,555 | 3/1969 | Mahnken | 260/583 |
| 4,247,480 | 1/1981 | Murata et al. | 564/298 |
| 4,889,954 | 12/1989 | Laurenzo et al. | 564/298 |
| 4,970,340 | 11/1990 | Smith | 564/298 |
| 5,583,258 | 12/1996 | Hawkins | 564/298 |

FOREIGN PATENT DOCUMENTS

| | | |
|---|---|---|
| 0 037 996 | 10/1981 | European Pat. Off. . |
| 3014510 | 10/1981 | Germany . |
| 30 14 510 A1 | 10/1981 | Germany . |
| 3014510 C2 | 10/1981 | Germany . |
| 3014510 | 9/1982 | Germany . |

*Primary Examiner*—Peter O'Sullivan
*Attorney, Agent, or Firm*—Connolly and Hutz

[57] ABSTRACT

Process for the preparation of tertiary amine oxides by reaction of a tertiary amine with a compound which splits off oxygen. To avoid gel and foam formation, a portion of the amine oxide to be prepared is added before the start of this reaction.

13 Claims, No Drawings

PROCESS FOR THE PREPARATION OF TERTIARY AMINE OXIDES

The reaction of tertiary amines, for example of the fatty alkyl-dimethylamine or di-fatty alkyl-methylamine type, with an aqueous hydrogen peroxide solution gives the corresponding tertiary amine oxides. Such amine oxides are surfactants which are not sensitive to water hardness, have good foaming properties and irritate the skin little and are therefore used as constituents of cleaning compositions and body care compositions.

The processes known to date for the preparation of tertiary amine oxides relate to improvement in the yield, reduction in the content of nitrosamine and avoidance of troublesome gel phases during preparation.

In the process from U.S. Pat. No. 4,247,480, high yields of tertiary amine oxide are achieved by carrying out the oxidation of the tertiary amine with an aqueous hydrogen peroxide solution in the presence of 0.01 to 2% by weight of carbon dioxide, based on the amine employed, and if appropriate in the presence of tetraacetylethylenediamine, a salt thereof, polyphosphates, stannates, a hydroxycarboxylic acid salt or the salt of a polycarboxylic acid. A 5 to 70% strength by weight aqueous hydrogen peroxide solution is preferably employed, either an amount of hydrogen peroxide stoichiometric to the amine or, preferably, an excess of 5 to 10% being used. The reaction is carried out at a temperature in the range from 40° to 80 °C.

In U.S. Pat. No. 3,283,007, the use of a small amount of pentaacetyl-diethylenetriamine during the oxidation of tertiary amines contaminated with heavy metals is recommended to improve the yield. The hydrogen peroxide solution employed has a concentration of at least 20% by weight of hydrogen peroxide, preferably 30 to 75% by weight, and the reaction temperature is in the range from 40° to 80° C.

With the process according to U.S. Pat. No. 4,889,954, tertiary amines can be reacted in high yields to give the corresponding amine oxides with a low content of nitrosamines, the oxidation of the tertiary amine being carried out in the presence of a dialkyl-carboxylic acid ester as the catalyst and, if appropriate, ascorbic acid as a co-catalyst. Suitable aqueous hydrogen peroxide solutions have a concentration of 3 to 90% by weight of hydrogen peroxide. An amount of hydrogen peroxide which is at least stoichiometric is required, and 1 to 5 mol, in particular 1 to 1.5 mol, of hydrogen peroxide per mole of tertiary amine is preferred. The reaction temperature can be chosen within a relatively wide temperature range, usually in a range from 0° to 100° C.

Various possible solutions are described in the prior art for avoiding the gel phases which occur during the preparation of tertiary amine oxides.

According to U.S. Pat. No. 3,215,741, the occurrence of gel phases is observed if hydrogen peroxide solutions having a concentration in the range from 20 to 90% by weight of hydrogen peroxide are used at a reaction temperature in the range from 40° to 80° C., and these can be avoided by simultaneous addition of an adequate amount of water during the oxidation of the tertiary amine.

According to U.S. Pat. No. 3,432,555, the formation of gel phases can be avoided by first heating the mixture of amine, water and a complexing agent, for example pentaacetyldiethylenetriamine, to a temperature of 85° to 115° C. and then adding at least the stoichiometric amount of an aqueous hydrogen peroxide solution, with an exothermic rise in temperature.

According to EP-A-0 230 510, to avoid gel formation during the preparation of di-$C_6$–$C_{20}$-alkylmethylamine oxide, the oxidation of the tertiary amine on which the product is based is carried out with at least the stoichiometric amount of an at least 40% strength by weight hydrogen peroxide solution. DE-A-30 14 510 describes a process for the preparation of naphthenoylamino-alkylene-dialkyl-amine oxides in which the amine on which the product is based is oxidized in the form of an aqueous, finely divided 20 to 40% strength by weight dispersion which, if appropriate, comprises 0.5 to 5% by weight, based on the dispersion, of the corresponding amine oxide, at a temperature above 70° C. using a compound which splits off oxygen, for example aqueous hydrogen peroxide solution. It has been found that the use of an aqueous, finely divided dispersion of the amines allows the reaction time required for the oxidation to be greatly shortened. 0.5 to 5% by weight of an aqueous solution of the amine oxide to be prepared can be added for additional stabilization of the dispersion.

Severe foam formation may occur when the reaction starts during preparation of tertiary amine oxides. There is thus both the risk of foaming over as a result of the exothermic reaction and the risk of uncontrolled decomposition of the hydrogen peroxide employed.

The object of the present invention is to provide a process for the preparation of tertiary amine oxides without the abovementioned disadvantages of the inadequate yield and the gel and foam formation.

Surprisingly, it has been found that by addition of tertiary amine oxide during the oxidation of a tertiary amine with a compound which splits off oxygen, the occurrence of the abovementioned disadvantages during the preparation process can be suppressed.

The present invention relates to a process for the preparation of tertiary amine oxides of the formula I

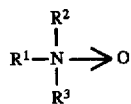

in which $R^1$ is $C_1$–$C_3$-alkyl, $R^2$ is $C_1$–$C_{20}$-alkyl and $R^3$ is $C_6$–$C_{22}$-alkyl, by reaction of a tertiary amine of the formula II

with a compound which splits off oxygen, which comprises carrying out the reaction in the presence of 1 to 15% by weight, based on the reaction mixture of a tertiary amine oxide of the formula I, preferably of the tertiary amine oxide to be prepared.

In the amines of the formula II, $R^1$ is preferably methyl or ethyl, $R^2$ is $C_1$–$C_{12}$-alkyl and $R^3$ is $C_8$–$C_{20}$-alkyl. Examples which may be mentioned are: octyldimethylamine, dodecyldimethylamine, tetradecyldimethylamine, hexadecyldimethylamine, octadecyldimethylamine, eicosyldimethylamine, dioctylmethylamine, didecylmethylamine and didodecylmethylamine. The amines of the formula II can be employed as individual compounds or in the form of a synthetic or naturally occurring mixture, such as, for example, coconut-dimethylamine.

Hydrogen peroxide, alkali metal hypochlorite or inorganic or organic peracids are used as the compounds which split off oxygen. The use of hydrogen peroxide is preferred. The use of an aqueous hydrogen peroxide solution is particularly preferred. The concentration of the aqueous hydrogen peroxide solution can be chosen within a wide range and comprises solutions having a concentration in the range from 3 to 90% by weight of hydrogen peroxide. The concentration is preferably 20 to 70% by weight, in particular 20 to 40% by weight, of hydrogen peroxide. The amount of hydrogen peroxide employed corresponds to at least the stoichiometric amount of amine employed. 1–1.5 mol of hydrogen peroxide per mole of amine of the formula II is preferred, particularly preferably 1.01–1.1 mol. Any excess of hydrogen peroxide can be eliminated by addition of a reducing agent or of an agent which destroys hydrogen peroxide after the reaction has been carried out. If necessary, complexing agents, such as EDTA, can be added, depending on the purity of the amine employed.

The reaction according to the invention can be carried out in a wide temperature range. The temperature is to be chosen such that on the one hand a satisfactory rate of reaction is achieved, and on the other hand the starting substances employed and the products obtained are not decomposed. The temperature range usually extends from 0° to 100° C., preferably 30° to 900° C., particularly preferably from 45° to 85° C.

The process according to the invention can be carried out in the customary stirred containers used in the chemical industry. In view of the fact that the foam formation which has occurred in the processes customary to date is suppressed, there are many diverse embodiments for the process according to the invention. It is thus possible to add the oxygen-containing compound to the amine and the amine oxide at elevated temperature in the range from 60° to 900° C. without risk. It can be added either all at once or in portions.

In another process variant, the amine, amine oxide and oxygen-containing compound are introduced into the reaction vessel and are heated to the required reaction temperature. The start of the reaction here is controlled and no foam or gel formation occurs.

In the course of the oxidation, a clear to slightly opalescent solution of the amine oxide of the formula I is formed. The solutions have a varying viscosity, which can be classified as thinly liquid to medium, depending on the content of amine oxide in the solutions. No gelatinous to high-viscosity solutions are formed. Advantageously, no foam formation occurs when carrying out the process according to the invention, which in turn allows a controlled reaction procedure and the optimum utilization of the reaction tank used in respect of the largest possible amount of starting substances. Furthermore, the formation of tertiary amine oxides with a reduced nitrosamine content is achieved with the process according to the invention.

PREPARATION EXAMPLES

EXAMPLE 1

3948 kg of dimethylmyristylamine, 9078 kg of water, 1000 kg of dimethyllaurylamine oxide (25% strength by weight) and 2 kg of EDTA are mixed in a stirred tank and heated to 80° C., and 1612 kg of aqueous hydrogen peroxide solution (35% strength by weight) are then added in the course of 2 hours. The reaction mixture is kept at a temperature of 80° to 82° C. over a period of 8 hours.

Neither foam formation nor gel formation occurs during the reaction. For this reason, the amount of substance reacted is 50% above that in the reaction carried out for comparison without addition of amine oxide. The reaction time is 30% below the time span required in the corresponding comparison experiment. The nitrosamine content is 50% lower. The content of unreacted amine and hydrogen peroxide is very low at 0.5% and 0.05% respectively. The hydrogen peroxide excess required for the reaction is 1%.

EXAMPLE 2

2570 kg of dimethyllaurylamine, 5000 kg of water, 2 kg of EDTA, 500 kg of dimethyllaurylamine oxide and 1100 kg of aqueous hydrogen peroxide solution (35% strength by weight) are mixed at about 30° C. and heated at a temperature rate of 0.5° C./minute. The reaction starts in a controlled manner at about 45° C., with a controllable rise in temperature of 0.3° C./minute. The reaction is carried out at the abovementioned temperature with cooling. No foam formation or gel formation occurs. In a comparison experiment carried out in a corresponding manner without addition of amine oxide, the reaction first starts at a temperature 10° C. higher at more than twice the rate, so that a controlled reaction procedure is not ensured.

EXAMPLE 3

Procedure corresponding to Example 2

Half the aqueous hydrogen peroxide solution is added at a temperature of 60° C. The reaction starts without problems with a controllable increase in temperature to about 85° C. in about 1.5 hours. After cooling to approximately 60° C., the second half of the hydrogen peroxide solution is added. No foam or gel formation is to be observed. The tank employed can be utilized to its full extent.

We claim:

1. A process for the preparation of a tertiary amine oxide of the formula I

(I)

in which

R$^1$ is C$_1$–C$_3$-alkyl,

R$^2$ is C$_1$–C$_{20}$-alkyl and

R$^3$ is C$_6$–C$_{22}$-alkyl, by reaction of a tertiary amine of the formula II

(II)

with a compound which splits off oxygen, which comprises carrying out the reaction in the presence of 1 to 15% by weight, based on the reaction mixture of a tertiary amine oxide of the formula I wherein essentially all of said tertiary amine oxide is present in the reaction mixture before the reaction starts.

2. The process as claimed in claim 1, wherein the preparation is carried out in the presence of the tertiary amine oxide to be prepared.

3. The process as claimed in claim 1, wherein R$^1$ is methyl or ethyl, R$^2$ is C$_1$–C$_{12}$-alkyl and R$^3$ is C$_8$–C$_{20}$-alkyl.

4. The process as claimed in claim 1, wherein hydrogen peroxide, alkali metal hypochlorite, an inorganic peracid or an organic peracid is employed as the compound which splits off oxygen.

5. The process as claimed in claim 1, wherein an aqueous hydrogen peroxide solution is employed.

6. The process as claimed in claim 1, wherein a 3 to 90% strength by weight hydrogen peroxide solution is employed.

7. The process as claimed in claim 1, wherein 1–1.5 mol of hydrogen peroxide per mole of amine of the formula II are employed.

8. The process as claimed in claim 1, wherein the reaction is carried out at a temperature in the range from 0° to 100° C.

9. The process claimed in claim 1, wherein a 20 to 70% strength by weight hydrogen peroxide solution is employed.

10. The process as claimed in claim 1, wherein a 20 to 40% by weight hydrogen peroxide solution is employed.

11. The process as claimed in claim 1, wherein 1.01–1.1 mol of hydrogen peroxide per mole of amine of the formula II are employed.

12. The process as claimed in claim 1, wherein the reaction is carried out at a temperature in the range from 30° to 90° C.

13. The process as claimed in claim 1, wherein the reaction is carried out at a temperature in the range from 45° to 85° C.

* * * * *